United States Patent
Choi et al.

(10) Patent No.: US 12,278,012 B2
(45) Date of Patent: Apr. 15, 2025

(54) SYSTEM AND METHOD FOR DETECTION OF IMPAIRMENT IN COGNITIVE FUNCTION

(71) Applicant: The Hong Kong Polytechnic University, Kowloon (HK)

(72) Inventors: Kup Sze Choi, Kowloon (HK); Xiao Shen, Kowloon (HK)

(73) Assignee: The Hong Kong Polytechnic University, Hong Kong (CN)

( * ) Notice: Subject to any disclaimer, the term of this patent is extended or adjusted under 35 U.S.C. 154(b) by 1073 days.

(21) Appl. No.: 17/196,626

(22) Filed: Mar. 9, 2021

(65) Prior Publication Data

US 2022/0293266 A1 Sep. 15, 2022

(51) Int. Cl.
| | | |
|---|---|---|
| G06N 3/08 | (2023.01) | |
| G06N 3/045 | (2023.01) | |
| G16H 10/60 | (2018.01) | |
| G16H 50/20 | (2018.01) | |

(Continued)

(52) U.S. Cl.
CPC ............. *G16H 50/20* (2018.01); *G06N 3/045* (2023.01); *G06N 3/08* (2013.01); *G16H 10/60* (2018.01); *G16H 50/30* (2018.01); *G16H 50/70* (2018.01)

(58) Field of Classification Search
CPC ........ G16H 50/20; G16H 10/60; G16H 50/30; G16H 50/70; G06N 3/045; G06N 3/08; G06N 3/048; G06N 5/01; G06N 20/10; G06N 20/20
See application file for complete search history.

(56) References Cited

U.S. PATENT DOCUMENTS

| | | | |
|---|---|---|---|
| 2019/0065284 A1* | 2/2019 | Sardino | G06F 9/5027 |
| 2019/0304092 A1* | 10/2019 | Akselrod-Ballin | G06N 3/084 |
| 2021/0158156 A1* | 5/2021 | Shamir | G06N 3/045 |

(Continued)

OTHER PUBLICATIONS

Zhou, Tao, et al. "Effective feature learning and fusion of multimodality data using stage-wise deep neural network for dementia diagnosis." Human brain mapping 40.3 (2019): 1001-1016. (Year: 2019).*

(Continued)

*Primary Examiner* — Michael J Huntley
*Assistant Examiner* — Sehwan Kim
(74) *Attorney, Agent, or Firm* — Millen, White, Zelano & Branigan P.C.; Wan-Ching Montfort

(57) ABSTRACT

A machine learning method predicts whether a specified subject is at high risk of developing cognitive impairment based upon a data record for said specified subject, and a method of training a dual neural network for such. These methods may work by automatically classifying said subject into a first class associated with a first predicted risk of cognitive impairment or a second class associated with a second predicted risk of cognitive impairment. Subject records are obtained comprising a first set of measured data and a second set of data including results for two or more health assessment questionnaires; and a label indicating that the subject belongs to the first class or second class. These records are used to train first and second neural networks, and in the latter method these trained networks are able to predict whether a specified subject should belong to said first class or second class.

13 Claims, 8 Drawing Sheets

(51) Int. Cl.
   *G16H 50/30* (2018.01)
   *G16H 50/70* (2018.01)

(56) References Cited

U.S. PATENT DOCUMENTS

2021/0256295 A1* 8/2021 Matsumoto .......... G06V 10/809
2021/0406603 A1* 12/2021 Narwariya .......... G06F 18/2148
2022/0084675 A1* 3/2022 Al-Ghoul ............... G06N 20/00

OTHER PUBLICATIONS

Joshi, Sandhya, et al. "Evaluation of different stages of dementia employing neuropsychological and machine learning techniques." 2009 First International Conference on Advanced Computing. IEEE, 2009. (Year: 2009).*
Beretta, Lorenzo, and Alessandro Santaniello. "Nearest neighbor imputation algorithms: a critical evaluation." BMC medical informatics and decision making 16 (2016): 197-208. (Year: 2016).*
Ho, Yaoshiang, and Samuel Wookey. "The real-world-weight cross-entropy loss function: Modeling the costs of mislabeling." IEEE access 8 (2019): 4806-4813. (Year: 2019).*
Rana, Sijan S., et al. "A multi-modal deep learning approach to the early prediction of mild cognitive impairment conversion to Alzheimer's disease." 2020 IEEE/ACM International Conference on Big Data Computing, Applications and Technologies (BDCAT). IEEE, 2020. (Year: 2020).*
Livingston G, Sommerlad A, Orgeta V, Costafreda SG, Huntley J, Ames D, et al. Dementia prevention, intervention, and care. The Lancet Dec. 2017;390(10113):2673-2734. [doi: 10.1016/S0140-6736(17)31363-6.
Kivipelto M, Mangialasche F, Ngandu T. Lifestyle interventions to prevent cognitive impairment, dementia and Alzheimer disease. Nat Rev Neurol Nov. 2018;14(11):653-666. [doi: 10.1038/s41582-018-0070-3] [Medline: 3029131].
Amjad H, Roth DL, Sheehan OC, Lyketsos CG, Wolff JL, Samus QM. Underdiagnosis of Dementia: an Observational Study of Patterns in Diagnosis and Awareness in US Older Adults. J Gen Intern Med Jul. 2018;33(7):1131-1138 [Free Full text] [doi: 10.1007/s11606-018-4377-y] [Medline: 29508259].
Connolly A, Gaehl E, Martin H, Morris J, Purandare N. Underdiagnosis of dementia in primary care: variations in the observed prevalence and comparisons to the expected prevalence. Aging Ment Health Nov. 2011; 15(8):978-984. [doi:10.1080/13607863.2011.596805] [Medline: 21777080].
Folstein M, Folstein S, McHugh P. "Mini-mental state". Journal of Psychiatric Research Nov. 1975;12(3):189-198. [doi:10.1016/0022-3956(75)90026-6].
Galasko D, Abramson I, Corey-Bloom J, Thal LJ. Repeated exposure to the Mini-Mental State Examination and the Information-Memory-Concentration Test results in a practice effect in Alzheimer's disease. Neurology Aug. 1993;43(8):1559-1563. [doi: 10.1212/wnl.43.8.1559] [Medline: 8351011] (ABST).
Agarwal V, Zhang L, Zhu J, Fang S, Cheng T, Hong C, et al. Impact of Predicting Health Care Utilization Via Web SearchBehavior: A Data-Driven Analysis. J Med Internet Res Sep. 21, 2016;18(9):e251 [Free Full text] [doi: 10.2196/ mir.6240][Medline: 27655225].
Maroco J, Silva D, Rodrigues A, Guerreiro M, Santana I, de Mendonça A. Data mining methods in the prediction of Dementia: A real-data comparison of the accuracy, sensitivity and specificity of linear discriminant analysis, logistic regression, neural networks, support vector machines, classification trees and random forests. BMC Res Notes Aug. 17, 2011;4:299 [Free Full text] [doi: 10.1186/1756-0500-4-299] [Medline: 21849043].
So A, Hooshyar D, Park K, Lim H. Early Diagnosis of Dementia from Clinical Data by Machine Learning Techniques. Applied Sciences Jun. 23, 2017;7(7):651. [doi: 10.3390/app7070651].
Cleret de Langavant L, Bayen E, Yaffe K. Unsupervised Machine Learning to Identify High Likelihood of Dementia in Population-Based Surveys: Development and Validation Study. J Med Internet Res Jul. 9, 2018;20(7):e10493 [Free Full text] [doi: 10.2196/10493] [Medline: 29986849].
Creavin ST, Wisniewski S, Noel-Storr AH, Trevelyan CM, Hampton T, Rayment D, et al. Mini-Mental State Examination (MMSE) for the detection of dementia in clinically unevaluated people aged 65 and over in community and primary care populations. Cochrane Database Syst Rev Jan. 13, 2016(1):CD011145. [doi: 10.1002/14651858. CD011145.pub2] [Medline:26760674].
Cleeland CS, Ryan KM. Pain assessment: global use of the Brief Pain Inventory. Ann Acad Med Singapore Mar. 1994;23(2):129-138. [Medline: 8080219].
Smith R. Validation and Reliability of the Elderly Mobility Scale. Physiotherapy Nov. 1994;80(11):744-747. [doi:10.1016/s0031-9406(10)60612-8].
Yesavage JA, Sheikh JI. 9/Geriatric Depression Scale (GDS). Clinical Gerontologist Oct. 25, 2008;5(1-2):165-173. [doi: 10.1300/J018v05n01_09].
Guigoz Y, Vellas B, Garry P. Mini nutritional assessment: a practical assessment tool for grading the nutritional state of elderly patients. In: Vellas BJ, Albarede L, Garry PJ, editors. Facts and Research in Gerontology. Paris: Serdi; 1994:15-60. (ABST).
Chan AO, Lam KF, Hui WM, Hu WH, Li J, Lai KC, et al. Validated questionnaire on diagnosis and symptom severity for functional constipation in the Chinese population. Aliment Pharmacol Ther Sep. 1, 2005;22(5):483-488 [Free Full text] [doi: 10.1111/j.1365-2036.2005.02621.x] [Medline: 16128687.
Jeni L, Cohn J, De LT. Facing imbalanced data—recommendations for the use of performance metrics. 2013 Presented at: The 2013 Humaine Association Conference on Affective Computing and Intelligent Interaction; Sep. 2-5, 2013; Geneva, Switzerland p. 245-251. [doi: 10.1109/acii.2013.47].
Zhang T. Solving large scale linear prediction problems using stochastic gradient descent algorithms. 2004 Presented at: The 21st International Conference on Machine learning; Jul. 4-8, 2004; Banff, Alberta, Canada. [doi:10.1145/1015330.1015332].
Weinberger KQ, Blitzer J, Saul LK. Distance metric learning for large margin nearest neighbor classification. 2005 Presented at: The 18th Annual Conference on Neural Information Processing Systems; Dec. 5-8, 2005; Vancouver, British Columbia, Canada.
Felsenstein J. An alternating least squares approach to inferring phylogenies from pairwise distances. Syst Biol Mar. 1997;46(1):101-111. [doi: 10.1093/sysbio/46.1.101] [Medline: 11975348].
Shen X, Dai Q, Chung F, Lu W, Choi K. Adversarial Deep Network Embedding for Cross-Network Node Classification. Apr. 3, 2020 Presented at: The 34th Conference on Artificial Intelligence; Feb. 7-12, 2020; New York, USA p. 2991-2999. [doi: 10.1609/aaai.v34i03.5692.

* cited by examiner

Algorithm 2: Dual Neural Network
Input:
Client profile features, health assessment features and ground-truth labels of training samples $\{p_i, q_i, y_i\}_{i=1}^{m_r}$; client profile features and health assessment features of testing samples $\{p_i, q_i\}_{i=1}^{m_e}$; hidden dimensionalities of neural network $d_1, d_2$. ⸺ 52

Fill missing values by imputation to yield a dataset of compete features. ⸺ 54
while not *maximum iteration* do:
    Given $\{p_i\}_{i=1}^{m_r}$ as input, learn the deepest latent profile representations $\{h_i^{p(2)}\}_{i=1}^{m_r}$ with NN1; ⸺ 56

Given $\{q_i\}_{i=1}^{m_r}$ as input, learn the deepest latent health assessment representations $\{h_i^{q(2)}\}_{i=1}^{m_r}$ with NN2; ⸺ 58

Concatenate $\{h_i^{p(2)}\}_{i=1}^{m_r}$ and $\{h_i^{q(2)}\}_{i=1}^{m_r}$ to obtain the final representations $\{h_i\}_{i=1}^{m_r}$; ⸺ 60

Based on the final representations and the ground-truth labels of training samples $\{h_i, y_i\}_{i=1}^{m_r}$, update the trainable parameters to minimize (8) by SGD; ⸺ 62
end while Given $\{p_i, q_i\}_{i=1}^{m_e}$ as input, use the optimized representation learning parameters to generate the final representations for the testing samples $\{h_i\}_{i=1}^{m_e}$; ⸺ 64

Apply the optimized classification parameters on $\{h_i\}_{i=1}^{m_e}$ to obtain the probabilities of high-risk cases for the testing samples $\{\hat{y}_i\}_{i=1}^{m_e}$. ⸺ 66

Output: ⸺ 68
Probabilities of high-risk cases for the testing samples $\{\hat{y}_i\}_{i=1}^{m_e}$.

Fig. 1B

Algorithm 1: KNN Imputation

Input:

Complete features $C = \{c_l\}_{l=1}^{n_c}$, incomplete features $S = \{s_b\}_{b=1}^{n_s}$, and number of nearest neighbors $k$. ⟵ 91

Measure distance between each pair of client records based on $C$ and get distance matrix $D$; ⟵ 92 for each incomplete feature $b$:
    for each client record $i$ with missing feature value: ⟵ 94
        (a) Based on $D$, find the $k$ nearest neighbors of record $i$ among the records with feature $b$ containing a value, i.e., $KNN(i,b)$;
        (b) Fill the missing value of feature $b$ for record $i$ by putting more weight on closer neighbors, i.e., ⟵ 96
$$\hat{s}_{bi} = \sum_{j \in KNN(i,b)} \frac{D_{ij}^{-1}}{\sum_{j \in KNN(i,b)} D_{ij}^{-1}} s_{bj};$$
    end
end

Output: ⟵ 98

Imputed incomplete features $\hat{S} = \{\hat{s}_b\}_{b=1}^{n_s}$.

Fig. 2B

SYSTEM AND METHOD FOR DETECTION OF IMPAIRMENT IN COGNITIVE FUNCTION

FIELD OF THE DISCLOSURE

The present disclosure relates to a machine learning based method, training method and machine readable medium for detecting impairment in cognitive function, particularly for the early detection of people with high dementia risk.

BACKGROUND OF THE DISCLOSURE

Dementia is a collective term referring to a group of diseases that cause a decline in cognitive function owing to brain cell damage. The symptoms include degradation in memory, communication, or reasoning ability, which can seriously interfere with activities of daily living Dementia is more common as people grow older, although dementia is not a normal part of aging.

Recent studies have revealed lifestyle behavioral risk factors that can be modified to reduce the risk of dementia. It has been reported that 35% of dementia cases are attributable to modifiable risk factors, such as hypertension, obesity, depression, and smoking, which concern physical, cognitive, and social inactivity and can be countered through lifestyle interventions. As modification of lifestyle takes time, early identification of people with high dementia risk is important for intervention and support.

However, underdiagnosis of dementia at the early stage is common since the symptoms are subtle and the progression of cognitive impairment is insidious and cannot be easily observed by the person, family members, or even health care professionals.

In primary care, cognitive impairment is a diagnostic criterion of dementia, cognitive assessment tools are used to screen for clinically unevaluated cases. For example, the Mini-Mental State Examination (MMSE) is a commonly used tool for screening cognitive impairment, having a test result which is regarded as providing a strong diagnostic criterion of dementia. However, as MMSE is a questionnaire that is administered when symptoms of memory decline have occurred, early administration at the asymptomatic stage or repeated measurements can give erroneous results in view of a practice effect (the questions could be remembered). This means that the effectiveness of MMSE when used at later stages is degraded.

An alternative approach following the advances in artificial intelligence, is the use of machine learning for the detection of dementia risk, particularly when causal connections with risk factors remain unclear. Approaches reported in the literature include applying machine learning techniques to the data collected from population or community-based settings, such as the results of neuropsychology tests or physical examinations, to screen for people with high risk of dementia. Some supervised machine learning methods represent a majority, and they include naive Bayes, decision tree (DT), random forest (RF), artificial neural network, and support vector machine (SVM), whereas their unsupervised counterparts have also been exploited for dementia risk prediction.

However, missing data is a common problem with data collected from population or community-based settings which makes machine learning based approaches inaccurate and compromises their effectiveness at early identification of at risk people with symptoms of dementia. Data may be lost owing to noncompliance with appointment schedules, unwillingness to respond to specific questions, or inadvertence of interviewers; and such data is typically discarded from models leading to incomplete datasets. Another issue of data analysis in machine learning based approaches is class imbalance, where samples of the target (i.e. high-risk cases) and non-target (i.e. normal cases) are disproportionate. When learning from imbalanced data, supervised machine learning algorithms are usually overwhelmed by majority class examples which leads to an inaccurate model which gives rise to inappropriate conclusions.

It is an object of the present disclosure to provide an approach to the early detection of people with high risk of developing dementia, especially at the asymptomatic stage, which addresses or ameliorates at least some of the problems of the prior art based approaches, or at least provide the public with an alternative choice.

SUMMARY OF THE DISCLOSURE

Features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims.

In accordance an aspect of the present disclosure, there is provided a machine learning method for predicting whether a specified subject is at high risk of developing cognitive impairment based upon a data record for said specified subject by automatically classifying said subject into a first class associated with a first predicted risk of cognitive impairment or a second class associated with a second predicted risk of cognitive impairment; wherein the method comprises acquiring a plurality of subjects' records wherein each record comprises a first set of measured data and a second set of data including results for two or more health assessment questionnaires; and a label indicating that the subject belongs to the first class or second class;

automatically classifying subjects of the plurality of subjects into said first class or second class according to the label;

training a first and second neural network together on the plurality of subjects' records by generating latent representations thereof by iteratively;

(i) generating by the first neural network generating a latent representation of the first data set for a subject; and (ii) generating by the second neural network a latent representation for the subject's second data set; and (iii) concatenating said latent representations together and using said concatenated representations as inputs to a classifier configured for assigning said subject's record to either said first class or second class;

(iv) updating trainable parameters of the first and second neural networks and the classifier used for generation and evaluation of the latent representations of the subject's record by confirmation with a classification made according to the label for that subject's record;

predicting the risk of cognitive impairment for the specified subject by using the classifier to evaluate a concatenated vector of the latent representations generated by the trained first and second neural network respectively by assigning of the specified subject by the classifier to said first class or said second class.

Optionally, the method may further comprise imputing incomplete data in before determining by the first neural network or the second neural network of the corresponding latent representation by using one or more of K-nearest neighbour imputation or mean imputation.

Such imputed incomplete data before determining by the respective neural network of the corresponding latent representation may be performed using K-nearest neighbour imputation wherein the set of the number of neighbours is specified as less than five.

Optionally, the method may further comprise including a cost sensitive learning weighting to increase sensitivity of detection when using said classifier for evaluating the concatenated latent representation of profile data and health assessment data and for updating the training parameters of said first and second neural networks.

The cost sensitive learning weighting $w_i$ associating with $i^{th}$ subject may be calculated according to:
$w_i = m_r^n/m_r^d$ if $y_i=1$ (high-risk case) and $w_i=1$ if $y_i=0$ (normal case) and, $m_r^n$ and $m_r^d$ are the numbers of normal cases and high-risk cases in the training samples, respectively.

A classification loss function L of the classifier may be calculated according to:

$$\left| L = -\frac{1}{m_r} w_i \sum_{k=1}^{m_r} (1-y_i)\log(1-\hat{y}_i) + y_i \log(\hat{y}_i) \right|,$$

where $m_r$ is a number of training samples.

Advantageously, the first neural network has two hidden layers which are arranged determine a latent profile representation of said first set of data which is learned layer by layer as follows:

$h_i^{p(1)} = \text{ReLU}(p_i W^{p(1)} + b^{p(1)})$ $h_i^{p(2)} = \text{ReLU}(h_i^{p(1)} W^{p(2)} + b^{p(2)})$ where ReLU (·) is the rectified linear unit activation function characterized by ReLU(x)=max(0,x), $p_i$ is the input profile feature associated with subject i, $h^{p(1)} \in R^{1 \times d1}$ and $h^{p(2)} \in R^{1 \times d2}$ represent the latent profile representation of subject i, learned by the first and second hidden layers, respectively; and $d_1$ and $d_2$ are the dimensionality of the first and second hidden layers respectively; $W^{p(1)} \in R^{np \times d1}$ and $b^{p(1)} \in R^{1 \times d1}$ are the trainable parameters associated with the first hidden layer; and $W^{p(2)} \in R^{d1 \times d2}$ and $b^{p(2)} \in R^{1 \times d2}$ are the trainable parameters associated with the second hidden layer.

Preferably the second neural network has two hidden layers which are arranged to determine a latent representation of second set of data including results for two or more health assessment questionnaires, which is learned layer by layer as follows:

$h_i^{q(1)} = \text{ReLU}(q_i W^{q(1)} + b^{q(1)})$ $h_i^{q(2)} = \text{ReLU}(h_i^{q(1)} W^{q(2)} + b^{q(2)})$ where $q_i$ is the feature of health assessment of subject i and $h_i^{q(1)} \in R^{1 \times d1}$ and $h_i^{q(2)} \in R^{1 \times d2}$ are the latent health assessment representations of subject i learned by the first and second hidden layers and $W^{q(1)} \in R^{nq \times d1}$, $b^{q(1)} \in R^{1 \times d1}$, $W^{q(2)} \in R^{d1 \times d2}$, and $b^{q(2)} \in R^{1 \times d2}$ are the trainable parameters.

Advantageously a stochastic gradient descent algorithm is used without normalisation to determine the trainable parameters of said first and second neural networks.

Preferably, the dimensions of the first and second neural network are the same.

Advantageously, the first set of measured data in a subject record includes a plurality of data selected from the groups including:
demographic information of elderly subjects comprising gender, age, marital status, type of residency, relationship with roommates, and social participation;
measurements conducted on the subject selected from the group comprising body temperature, pulse rate, oxygen saturation, blood pressure, and waist-hip ratio; and
medical history selected from the group comprising records of health problems or past diseases.

The second set of measured data in a subject record may include results selected from the group of health assessment questionnaires comprising Brief Pain Inventory, Elderly Mobility Scale, Geriatic Depression Scale, Mini Nutrition Assessment, Constipation questionnaire, Roper Logan Tierney questionnaire, gross oral hygiene assessment, visual acuity assessment, and a survey of favorite activities questionnaire.

Advantageously, the specified subject's record comprises a first set of measured data and a second set of data including results for two or more health assessment questionnaires.

There is also provided a machine learning method for training a first and second neural network to determine whether a specified subject is at high risk of developing cognitive impairment based upon a data record for said specified subject; the method comprising
acquiring for a plurality of subjects a data record for the subjects, said data record including a first set of measured data and a second set of data including responses to two or more health assessment questionnaires; and a label indicating that the subject belongs to the first class or second class;
automatically classifying each subject of the plurality of subjects into said first class or second class according to the label;
training a first and second neural network together on the plurality of subjects' records by generating latent representations thereof by iteratively;
(i) generating by the first neural network generating a latent representation of the first data set for a subject; and
(ii) generating by the second neural network a latent representation of the second data set of the subject; and
(iii) concatenating said latent representations together and using said concatenated representations as inputs to a classifier configured for assigning said subject's record to either said first class or second class;
(iv) updating the trainable parameters of the first and second neural networks and the classifier used for generation and evaluation of the latent representations of the subject's record by confirmation with a classification made according to the label for that subject's record.

In yet a further aspect there is provided tangible non transitory computer readable medium comprising instructions executable by a processor for executing a process of predicting whether a specified subject is at high risk of developing cognitive impairment based upon a data record for a specified subject by automatically classifying the specified subject into a first class associated with a first predicted risk of cognitive impairment or a second class associated with a second predicted risk of cognitive impairment; said data record for the specified subject including a first set of data and a second set of data including results for two or more health assessment questionnaires; the process comprising:

acquiring a plurality of subjects' records wherein each record comprises a first set of measured data and a second set of data including results for two or more health assessment questionnaires; and a label indicating that the subject belongs to the first class or second class;

automatically classifying each subject of a plurality of subjects into said first class or second class according to the label;

training a first and second neural network together on data of subjects of the plurality of subjects health comprising assessment dataset and profile data respectively by:
(i) generating by the first neural network generating a latent representation of the first data set for a subject;
(ii) generating by the second neural network a latent representation for the subject's second data set;
(iii) concatenating said latent representations together and using said concatenated representations as inputs to a classifier configured for assigning said subject's record to either said first class or second class;
(iv) updating trainable parameters of the first and second neural networks and the classifier used for generation and evaluation of the latent representations of the subject's record by confirmation with the classification made according to the label for that subject's record;

predicting the risk of cognitive impairment for the specified subject by using the classifier to evaluate a concatenated vector of the latent representations generated by the trained first and second neural network respectively by assigning of the specified subject by the classifier to said first class or said second class.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended Figures. Understanding that these Figures depict only exemplary embodiments of the disclosure and are not therefore to be considered to be limiting of its scope, the principles herein are described and explained with additional specificity and detail through the use of the accompanying Figures.

Preferred embodiments of the present disclosure will be explained in further detail below by way of examples and with reference to the accompanying Figures, in which separate neural networks are used to learn latent representations based on two separate groups of input features, profile data and health assessment data.

FIG. 1B depicts a schematic outline of the steps in the algorithm used in an embodiment of the present disclosure.

FIG. 2B depicts a schematic outline of the steps in an exemplary implementation of the KNN imputation algorithm for completing gaps in data according to an embodiment of the present disclosure.

DETAILED DESCRIPTION OF THE PREFERRED EMBODIMENTS

Various embodiments of the disclosure are discussed in detail below. While specific implementations are discussed, it should be understood that this is done for illustration purposes only. A person skilled in the relevant art will recognize that other components and configurations may be used without departing from the scope of the disclosure.

The disclosed technology addresses the need in the art for a method and system for detecting early signs of cognitive impairment which is able to operate with incomplete information.

Embodiments of the present disclosure may be provided as a computer program product, which may include a machine-readable storage medium embodying instructions, which may be used to program a computer (or other electronic devices) to perform a process.

The machine-readable medium may include, any one of fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/machine-readable medium suitable for storing electronic instructions (e.g., computer programming code, such as software or firmware).

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

According to various embodiments of the present disclosure, after the neural networks disclosed herein have been trained, they can be used to determine impairment in cognitive function in a subject, outputting a value indicative of the classification of a subject as being of high risk or normal risk or other appropriate classification.

Figure 1A:
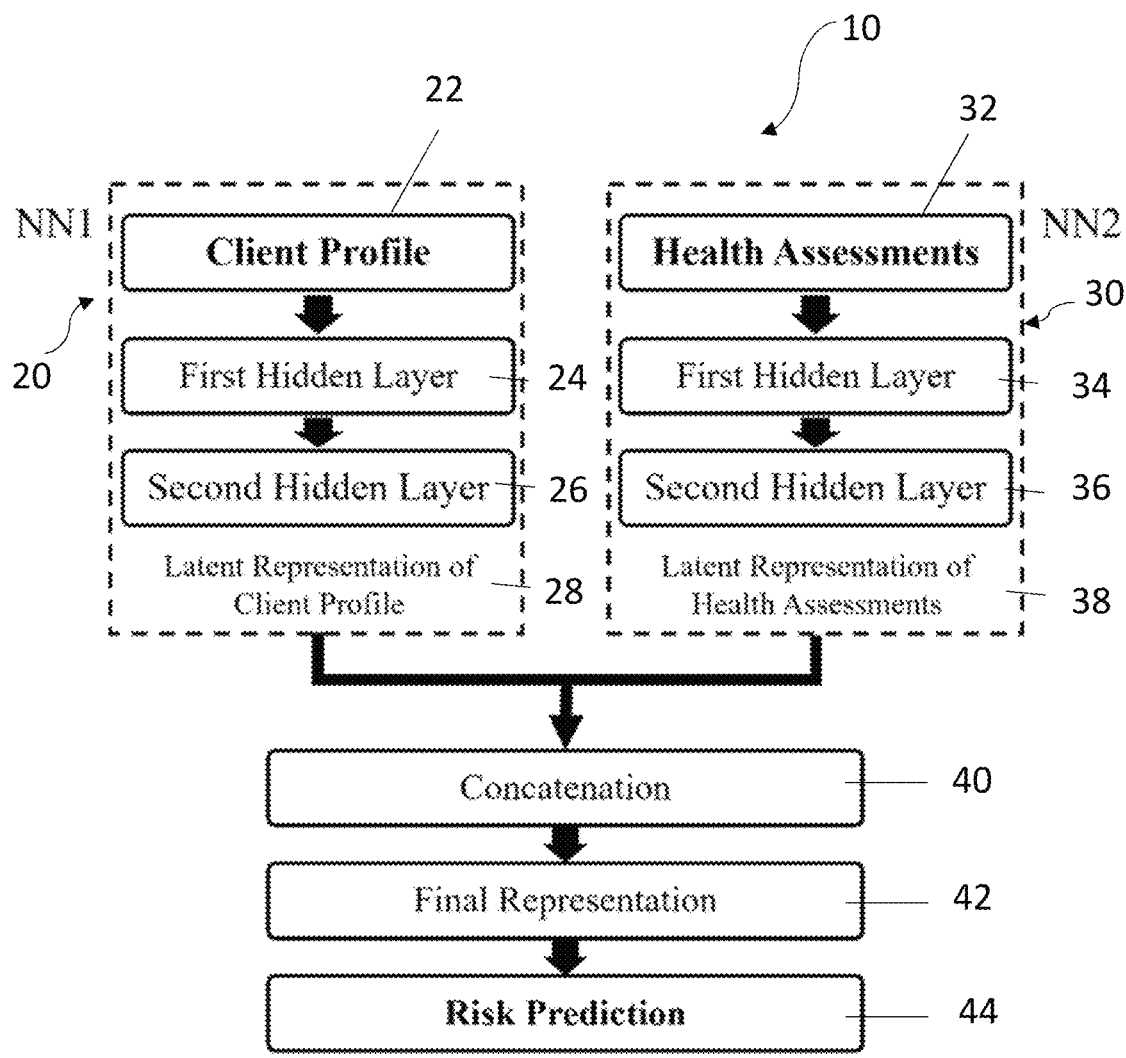
FIG. 1A depicts an exemplary schematic conceptual diagram showing the steps in the process of using the dual neural network based approach of the present disclosure with separate neural networks being trained on evaluating profile data and health assessment data.

FIG. 1A depicts an exemplary schematic conceptual diagram showing the steps in the process of using the dual neural network based approach of the present disclosure with separate neural networks being trained on evaluating profile data and health assessment data.

As depicted, in an exemplary embodiment of the present disclosure, two neural networks, namely, neural network 1 (NN1) 20 and neural network 2 (NN2) 30, each with two hidden layers 24, 26 and 34,36 respectively, learn the latent representations for each subject from the supplied profile data 22 and health assessment data 32 respectively.

Advantageously, the use of two hidden layers in the dual neural network approach described reduces the time complexity of neural network training and avoids overfitting, as compared to the use of additional hidden layers.

The representations are referred to respectively as latent profile representation 28 and latent health assessment representation 38.

The two latent representations 28,38 were then concatenated in step 40 to yield the final latent representation 42 of the data; which is then used for predicting the dementia risk 44 by evaluating whether this data was above a threshold level using a classifier.

Profile Data

Potentially useful profile data included objective data such as demographic information, medical history, and biological non-invasive measurements of the subjects.

In the present disclosure, the data set included demographic information of elderly subjects (eg, gender, age, marital status, type of residency, relationship with roommates, and social participation), bio-measurements (eg, body temperature, pulse rate, oxygen saturation, blood pressure, and waist-hip ratio), and medical history (eg, records of health problems or past diseases).

These fields may be continuous or categorical data that are advantageously obtained as early as possible upon visitation by a subject or client. Typically such data is measured or scored relatively objectively.

An exemplary listing of the data obtained for health care records includes measurements or scores for many of the following fields Age, Gender, temperature, systolic, diastolic, heart_rate, SpO2, PulseRate, body_weight, body_height, bmi, waist_hip_ratio, waist, hip, bioelectrical_impedance, trad_blood_glucose, Type_visit, Mobility, Participation, Marital_Status_ID, Housing_Type_ID, Living_Condition_ID, Living_With_Others_ID, Roomate_Relationship_ID, Financial, Loc_park, Loc_rest, Loc_shop, Loc_elder, Loc_other, Accid, T A, Slip, Burn, Accid_other, Ac_freq, AED, Hospital_Admission, Outpatient, Practitioner, Bone_Setter, T CM, Acupressure, Acupuncture, Smoking, Drinking, Education_ID, Independent_or_depend_on_fa mily, CSSA, Disability Allowance, Old Age Allowance, Cancer_Others, Cancer_Others—FollowUp, Cancer_Others—Drug, Heart Disease_Congestive Heart Disease, Heart Disease_Congestive Heart Disease—FollowUp, Heart Disease_Congestive Heart Disease—Drug, Heart Disease_Coronary Heart Disease, Heart Disease_Coronary Heart Disease—FollowUp, Heart Disease_Coronary Heart Disease—Drug, Heart Disease_Others, Heart Disease_Others—FollowUp, Heart Disease_Others—Drug, Chronic Lower Respiratory Diseases_Asthma, Chronic Lower Respiratory Diseases_Asthma—FollowUp, Chronic Lower Respiratory Diseases_Asthma—Drug, Chronic Lower Respiratory Diseases_COPD, Chronic Lower Respiratory Diseases_COPD—FollowUp, Chronic Lower Respiratory Diseases_COPD—Drug, Chronic Lower Respiratory Diseases_Others, Chronic Lower Respiratory Diseases_Others—FollowUp, Chronic Lower Respiratory Diseases_Others—Drug, Endocrine Disease_Hyperlipidaemia, Endocrine Disease_Hyperlipidaemia—FollowUp, Endocrine Disease_Hyperlipidaemia—Drug, Endocrine Disease_Diabetes Mellitus, Endocrine Disease_Diabetes Mellitus—FollowUp, Endocrine Disease_Diabetes Mellitus—Drug, Endocrine Disease_Others, Endocrine Disease_Others—FollowUp, Endocrine Disease_Others—Drug, Musculoskeletal Disorders_Gout, Musculoskeletal Disorders_Gout—FollowUp, Musculoskeletal Disorders_Gout—Drug, Musculoskeletal Disorders_Degenerative Joints, Musculoskeletal Disorders_Degenerative Joints—FollowUp, Musculoskeletal Disorders_Degenerative Joints—Drug, Musculoskeletal Disorders_Rheumatoid Arthritis, Musculoskeletal Disorders_Rheumatoid Arthritis—FollowUp, Musculoskeletal Disorders_Rheumatoid Arthritis—Drug, Musculoskeletal Disorders_Oesteoprosis, Musculoskeletal Disorders_Oesteoprosis—FollowUp, Musculoskeletal Disorders_Oesteoprosis—Drug, Musculoskeletal Disorders_Others, Musculoskeletal Disorders_Others—FollowUp, Musculoskeletal Disorders_Others—Drug, Peripheral Vascular Diseases_Varicose Veins, Peripheral Vascular Diseases_Varicose Veins—FollowUp, Peripheral Vascular Diseases_Varicose Veins—Drug, Peripheral Vascular Diseases_Others, Peripheral Vascular Diseases_Others—FollowUp, Peripheral Vascular Diseases_Others—Drug, Visual Impairment_Cataract, Visual Impairment_Cataract—FollowUp, Visual Impairment_Cataract—Drug, Visual Impairment_Others, Visual Impairment_Others—FollowUp, Visual Impairment_Others—Drug, Renal Disease_Others, Renal Disease_Others—FollowUp, Renal Disease_Others—Drug, GI Disorder_Gastric Ulcer, GI Disorder_Gastric Ulcer—FollowUp, GI Disorder_Gastric Ulcer—Drug, GI Disorder_Duodenal Ulcer, GI Disorder_Duodenal Ulcer—FollowUp, GI Disorder_Duodenal Ulcer—Drug, GI Disorder_Gastritis, GI Disorder_Gastritis—FollowUp, GI Disorder_Gastritis—Drug, GI Disorder_Piles, GI Disorder_Piles—FollowUp, GI Disorder_Piles—Drug, GI Disorder_Others, GI Disorder_Others—FollowUp, GI Disorder_Others—Drug, Malignant Neoplasm_Others, Malignant Neoplasm_Others—FollowUp, Malignant Neoplasm_Others—Drug, Medical_Illness_View_Others_Others, Others_Others—FollowUp, Others_Others—Drug This data may be obtained by elderly health care services such as registered nurses and advanced practice nurses or student nurses under supervision, who may also responsible for recording the data while conducting health assessments.

Health Assessment Data

Typically the same personnel recording profile data collect the health assessment data for subjects, with these typically representative of standardised approaches and based upon information reported by the subjects or clients themselves. Such data may be obtained just once, or on multiple occasions or appointments which are temporally separated, and may be recorded or conducted as needed by the personnel based upon their clinical evaluation of the need for such data/intervention in specific areas as required.

The health assessment data included in the present disclosure was information collected from nine health assessment questionnaires (ie, BPI, EMS, GDS, MNA, CQ, RLT, gross oral hygiene assessment, visual acuity assessment, and survey of favorite activities).

The data set adopted contained the results of different types of health assessments, which are described below.

It would be appreciated that other similar health assessment questionnaire type data could be utilised without departing from the scope or approach of the present disclosure such as Montreal Cognitive Assessment (MoCA), Abbreviated Mental Test (AMT), Berg Balance Scale (BBS), Time Up and Go Test, Visual Analogue Scale (VAS) for Pain, Thirty-Second Chair Stand Test, Pittsburgh Sleep Quality Index (PQSI), Happiness Questionnaire (HQ), Beck Depression Inventory (BDI), and World Health Organization Questionnaire on Quality of Life (WHOQOL).

(a) Mini-Mental State Examination

MMSE is a quick and reliable assessment of cognitive impairment in older adults. The use of MMSE as part of the process for diagnosing dementia is supported by a Cochrane review of 24,310 citations. MMSE consists of six sets of questions focusing on the cognitive aspects of mental function. For example, elderly subjects were asked to give the date of the day, perform arithmetic operations, and perform hand drawing. The assessment can be completed within 10 minutes. The maximum score is 30. A score between 24 and 30 indicates normal cognition, whereas a score below 24 suggests various degrees of impairment, with a lower score indicating greater impairment.

In this study, two-class classification was adopted (ie, normal [score $\geq 24$] and high-risk [score $<24$]), with the results from this classification (together with other relevant information) used in the training data as a way of verifying the assessment made by the dual neural networks from the provided health assessment data and other profile data for the training subjects as is discussed below.

(b) Brief Pain Inventory

The BPI is a questionnaire used to assess the severity of pain and its influence on elderly people. The short-form BPI was administered, and it has nine items concerning the location and degree of pain in the last 24 hours, treatments being applied, and their influences on functioning, such as walking ability, mood, and sleep.

(c) Elderly Mobility Scale

The EMS is a seven-item assessment tool used to evaluate the mobility of elderly people through functional tests (eg, transition between sitting and lying, gait, timed walk, and functional reach). The maximum score is 20. A score of 14 or above indicates normal mobility and independent living; a score between 10 and 13 indicates a borderline case; and a score below 10 indicates the necessity of assistance to perform activities of daily living.

(d) Geriatric Depression Scale

The GDS is a measure of depression in older adults. The short-form GDS was administered in the clinic. It contained 15 yes or no questions, each carrying one point, on the feeling about and attitude toward various aspects of life. The maximum score is 15. A score greater than five indicates depression.

(e) Mini-Nutrition Assessment

The MNA is a tool used to assess the nutritional status of older people. It is administered in two steps. The short form of MNA (MNA-SF), which has six items with a maximum score of 14, is first used to detect signs of decline in ingestion. The questions concern appetite loss, weight loss, and psychological stress in the last 3 months; mobility; and BMI. A score of 11 or below indicates possible malnutrition, and follow-up with the full MNA is required in the second step. The full MNA consists of 12 items with a maximum score of 16, and it involves further details such as independent living, medication, ulcers, diet, feeding modes, and mid-arm and calf circumference. The maximum total score of the MNA is 30, with a score below 17 indicating malnourishment.

(f) Constipation Questionnaire

The CQ is used to assess the severity of functional constipation. The questionnaire administered contains six items with questions concerning frequency of evacuation, difficulty to evacuate, incomplete evacuation, stool and abdominal symptoms, and medication.

(g) RLT-Based Questionnaire

Based on the RLT, a questionnaire with 36 items was designed to assess the independence of older adults in 12 categories of activities of daily living, including maintaining a safe environment, communication, breathing, eating and drinking, elimination, washing and cleaning, controlling body temperature, mobilization, working and playing, sleeping, expressing sexuality, and dying. The results of the questionnaire can be used to determine the interventions required to enable elderly people to remain independent in activities of daily living.

(h) Gross Oral Hygiene Assessment

The assessment tool consists of 20 items concerning various oral hygiene conditions of elderly subjects, including teeth cleansing, tooth decay, tooth mobility, denture use, denture care, missing or remaining teeth, calculus, gum bleeding, and oral candidiasis, with which the corresponding tooth locations and symptoms are recoded.

(i) Visual Acuity Assessment

Visual acuity of elderly subjects was measured at the mobile clinic. The data collected included the distance at which measurement was made, the visual aid used, and the results of measurements using the Snellen chart and the chart of the logarithm of the minimum angle of resolution (LogMAR chart).

(j) Survey of Favorite Activities

The survey involves binary yes or no questions, each recording a favorite activity of the elderly subjects. The questions cover a wide range of over 40 activities (eg, playing chess, watching television, listening to radio, fishing, hiking, calligraphy, dancing, and shopping).

This data was included in the Neural Networks in the architecture depicted in FIG. 1A in accordance with the algorithm depicted in FIG. 1B as follows.

In step 52, variables were assigned, specifically, $p_i \in R^{1 \times n_p}$ be a vector representing the profile information associated with subject i, where $n_p$ is the number of features in the profile.

The ground truth labels for the training samples are designated $y_i$, and represent the score on the MMSE evaluation.

Similarly, let $q_i \in R^{1 \times n_q}$ be a vector representing the health assessment information associated with subject i, where $n_q$ is the number of features in the assessment questionnaires.

Therefore, $n = n_p + n_q$ is the total number of input features.

Preferably in step 54, missing values of the input features were imputed before introduction into the model by the mean and K-nearest neighbour (KNN) imputation techniques described below.

In step 56, in neural network NN1, with the profile information as the input, the latent profile representation is learned layer by layer as follows:

$$h_i^{p(1)} = \text{ReLU}(p_i W^{p(1)} + b^{p(1)}) \quad (1)$$

$$h_i^{p(2)} = \text{ReLU}(h_i^{p(1)} W^{p(2)} + b^{p(2)}) \quad (2)$$

where ReLU(·) is the rectified linear unit activation function characterized by ReLU(x)=max(0,x), $p_i$ is the input profile feature associated with subject i, $h^{p(1)} \in R^{1 \times d1}$ and $h^{p(2)} \in R^{1 \times d2}$ represent the latent profile representation of subject i, learned by the first and second hidden layers of NN1, respectively, and $d_1$ and $d_2$ are the dimensionality of the first and second hidden layers of NN1, respectively.

Assign $W^{p(1)} \in R^{np \times d1}$ and $b^{p(1)} \in R^{1 \times d1}$ as the trainable weight and bias parameters associated with the first hidden layer of NN1.

Assign $W^{p(2)} \in R^{d1 \times d2}$ and $b^{p(2)} \in R^{1d \times d2}$ as the trainable parameters associated with the second hidden layer of NN1.

Similarly, in Step 58, in the neural network NN2, with the information from the health assessment as the input, the latent health assessment representation is learned layer by layer as follows:

$$h_i^{q(1)} = \text{ReLU}(q_i W^{q(1)} + b^{q(1)}) \quad (3)$$

$$h_i^{q(2)} = \text{ReLU}(h_i^{q(1)} W^{q(2)} + b^{q(2)}) \quad (4)$$

where $q_i$ is the feature of health assessment of subject i and $h_i^{q(1)} \in R^{1 \times d1}$ and $h_i^{q(2)} \in R^{1 \times d2}$ are the latent health assessment representations of subject i learned by the first and second hidden layers of NN2. Additionally, $W^{q(1)} \in R^{nq \times d1}$, $b^{q(1)} \in R^{1 \times d1}$, $W^{q(2)} \in R^{d1 \times d2}$, and $b^{q(2)} \in R^{1 \times d2}$ are the trainable parameters of NN2.

In the proposed DNN model, the hidden dimensionalities for NN1 and NN2 were set to be the same.

Thereafter, in step 60 the deepest latent profile representation learned by NN1 (ie, $h^{p(2)}$) and the deepest latent health assessment representation learned by NN2 (ie, $h_i^{q(2)}$) were concatenated to give the final representation as follows:

$$h_i = \text{Concat}(h_i^{p(2)}, h_i^{q(2)}) \quad (5)$$

where $h_i \in R^{1 \times 2d2}$ is the final representation of subject i.

In step 64 the final representation thus obtained is then provided into a classifier layer to predict whether an particular subject is determined to be in a high risk class or normal class according to the following function:

$$\hat{y}_i = \text{Softmax}(h_i W^y + b^y) \quad (6)$$

where $\hat{y}_i$ denotes the predicted probability that subject i is at high risk.

$W^y$ and $b^y$ are the trainable parameters associated with the dementia classification.

Given the ground truth labels of the subject records that are used as training samples, the supervised classification loss L is defined as follows:

$$\left| L = -\frac{1}{m_r} \sum_{i=1}^{m_r} (1 - y_i) \log(1 - \hat{y}_i) + y_i \log(\hat{y}_i) \right|, \quad (7)$$

where $m_r$ is the number of training samples.

The ground truth label is $y_i=1$ if the training sample corresponding to subject record i is a high-risk case and $y_i=0$ if it is a normal case, based in the training data on whether the MMSE exceeded a predetermined threshold.

In a further optional modification of the present disclosure; as the data set adopted in the study performed in the present disclosure was imbalanced, the classifiers in supervised machine learning could be biased toward the majority class samples (i.e., normal cases).

As a screening tool that is used to identify possible cases of high dementia risk, it is important to accurately detect the minority class (high-risk cases).

To make the proposed Dual Neural Network model focus more on high-risk cases, in step 62 a cost sensitive loss (CSL) method was employed by introducing the cost ratio w into the classification loss in equation 7 as follows:

$$\left| L = -\frac{1}{m_r} w_i \sum_{i=1}^{m_r} (1 - y_i) \log(1 - \hat{y}_i) + y_i \log(\hat{y}_i) \right|, \quad (8)$$

where $w_i = m_r^n/m_r^d$ if $y_i=1$ (ie, high-risk case) and $w_i=1$ if $y_i=0$ (ie, normal case). Additionally, $m_r^n$ and $m_r^d$ are the numbers of normal cases and high-risk cases in the training samples, respectively.

It is noted that $m_r^n$ is much larger than $m_r^d$, which means that $w_i$ is always larger than 1 if $y_i=1$. $m_r^n/m_r^d$ represents the ratio of weight on the high-risk case over that on the normal case. Setting a higher weight on the high-risk case makes the model yields higher classification loss when inaccurately identifying the ground-truth high-risk case than inaccurately identifying the ground-truth normal case. Then, in order to minimize the classification loss, the model would focus more on identifying the ground-truth high-risk cases than the ground-truth normal cases.

The trainable parameters of NN1 and NN2 that minimize the cost-sensitive classification loss in equation 8 were iteratively updated using the stochastic gradient descent (SGD) algorithm Let { } L denote the trainable parameters associated with NN1, { } denote the trainable parameters associated with NN2, and { } denote the trainable parameters associated with the classifier.

At each training epoch, the trainable parameters of NN1 and NN2 that minimize the cost-sensitive classification loss in equation 8 were iteratively updated using the stochastic gradient descent (SGD) algorithm as follows:

where denotes the learning rate. We set the initial learning rate as 1e-4, and decayed the learning rate by 0.95 after each 1000 iterations, and the maximum training iteration was set as 10000.

After the maximum training iteration has been reached, the latest updated trainable representation learning parameters and would be employed to generate the latent profile representation and latent health assessment representation via equations (1), (2), (3), (4). Then, we concatenated the latent profile representation and latent health assessment representation to get the final representation via equation (5). Next, we employed the latest updated trainable classification parameters to generate the predicted probability of an elderly client as the high-risk case via equation (6). Furthermore, in an additional preferable embodiment, it was observed that simply introducing either profile data or health assessment data into the neural networks in a raw form would lead to poor outcomes, as much of the data was incomplete. This can be understood with reference to the exemplary embodiment discussed in further detail below.

In order to address this deficiency, mean and KNN imputations were used in step 54 as noted above.

For mean imputation, the missing values of a record were filled by the average values of other records with observable feature values.

For the KNN imputation method, the missing values of each record were filled based on the observable values of its KNN. The idea is to assign a higher degree of importance to neighbors that are more similar to the target record when filling the missing values.

Figure 2A:
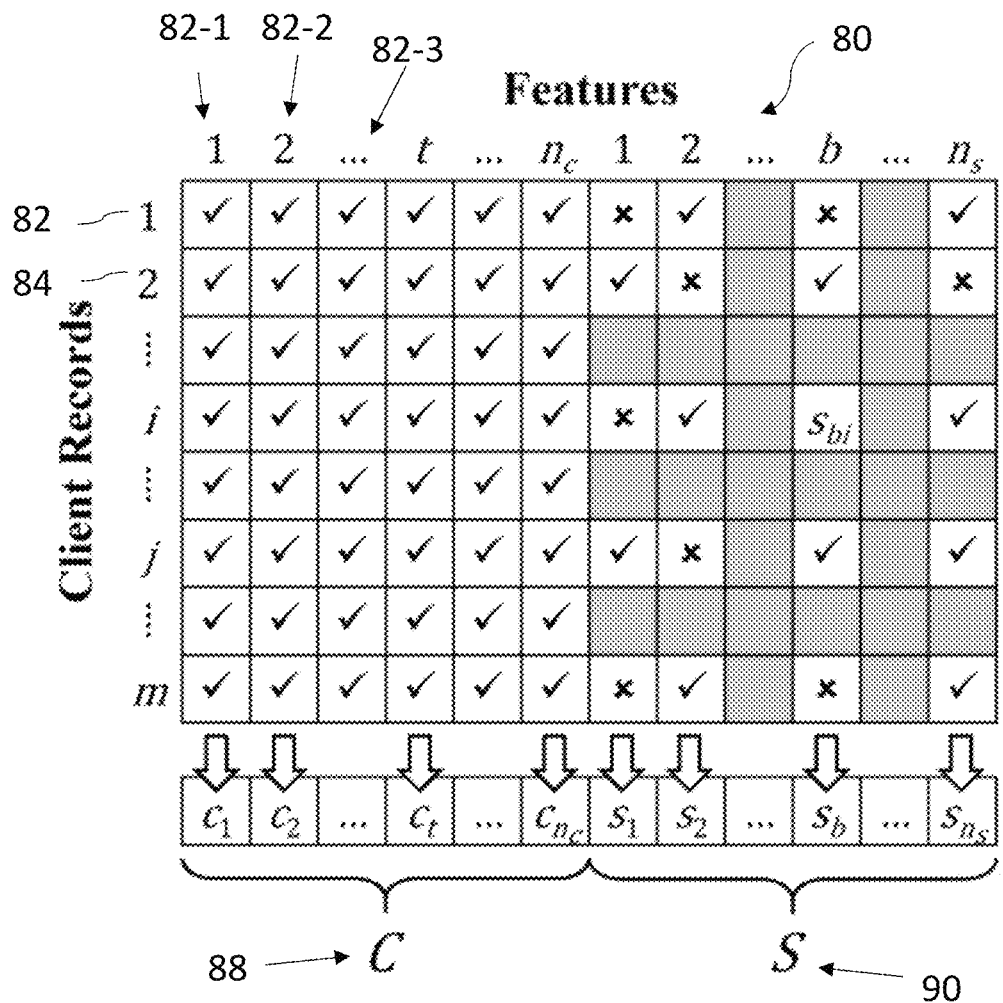
FIG. 2A depicts a schematic representation of the data and gaps therein, which is initially provided before use in the multiple neural network model of the present disclosure.

This can be seen conceptually by referring to FIG. 2A which is a schematic representation of the various data and gaps therein, which is initially provided before use in the multiple neural network model of the present disclosure.

As depicted the dataset 80 comprises a plurality of records 82,84,86 etc; each record including values for various data items 82.1, 82,.2, 82.3; 84.1.84.2, 84.3 etc; each of these data items being complete and having one or more values; or incomplete.

Where a specific record has data for a particular field which is complete, the record for that data item is indicated with a. "tick"; and where this data is missing, the record is indicated with a "X". The shaded region indicates the value may be either for the purposes of the abstraction depicted.

It can be seen then that the data may be divided into a "complete" set C (88) of particular data items, and an incomplete set of data items marked "S" (90).

The missing data may be "completed" or imputed, as outlined in further detail with reference to the flow chart shown in FIG. 2B.

Referring to FIG. 2B, in the algorithm depicted; variables are assigned as follows in step 91. let $C=\{c_t\}_{t=1}^{n_c}$ be the set of features with complete values for all records, denoted as complete features, and $S=\{s_b\}_{b=1}^{n_s}$ be the set of features with missing values, denoted as incomplete features, where $n_c$ and $n_s$ represent the number of complete and incomplete features, respectively. $c_t$ represents a complete feature where all the records in the data set have an entry value for the feature t.

By contrast, $s_b$ indicates an incomplete feature where at least one of the records in the data set does not provide an entry value for the feature b.

Furthermore, $s_{bi}$ represents the entry value of the feature b in record i, where $s_{bi}$ is null if the value of feature b in record i is missing.

Next, in step 92, Let $D \in R^{m \times m}$ be a distance matrix that measures the distance between each pair of records based on all complete features, where m is the number of records in the data set, and $D_{ij}$ represents the distance between records i and j. Optionally, Euclidean distance may be used as the distance metric; however, other distance metrics (eg, City Block Distance, Cosine similarity, L1 distance, L2 distance, and Manhattan distance [37,38]) can also be used.

Thus, the distance between each pair of records was measured based on all complete features.

Thereafter, the missing values of the incomplete features in a record were filled in steps 94,96 with the weighted average of the observable feature values of the k nearest records to that record. Specifically, for each record i with missing feature value (a) based upon D, in step 94, the K nearest neighbors of record i are found among the records with feature b containing a value ie.. KNN(i,b)); and in step 96 the missing value of feature b for record i by putting more weight on closest values is filled.

After imputation, all the features were treated as "complete" $S=\{s_b\}_{b=1}^{n_s}$ and then utilized as input features of the proposed model for dementia prediction as depicted in step 98.

Experimental Data

In an exemplary embodiment of the present disclosure the above methodology was applied and contrasted for comparative purposes with other prediction algorithms and is discussed in more detail below.

The data set used in the example contains the records of 2,299 elderly subjects, with one record per subject.

As noted above $n=n_p+n_q$ is the total number of input features.

In the provided data set, $n_p$ was 132, $n_q$ was 435, and n was 567. Therefore, each record has a total of 567 features that were the inputs of the models.

The data set was imbalanced, with 1,872 normal cases and only 427 high-risk cases, which was addressed using the CSL modification noted above.

The features originated from demographic data, bio-measurements, and medical history, as well as the data collected from the various health assessment questionnaires described above, except MMSE.

The scores of MMSE were utilized to generate the labels of the models in training mode. If the score of an elderly subject was lower than 24, the corresponding sample was labeled as a "high-risk case;" otherwise, the sample was labeled as a "normal case."

As shown in Table 1, among the 567 features, complete values were only available from 96 features for all 2,299 records. In addition, 49 features had a data missing rate of no more than 10% (ie, the values for these 49 features were missing in less than 10% of the records). The data missing rate of 140 features was over 60%. Furthermore, the data set was imbalanced, with 1,872 normal cases versus 427 high-risk cases.

In the data set adopted, the profile features were more complete than the health assessment features, that is, more than 72% of the profile features were complete, while all the features from the health assessment questionnaires contained missing values, with the missing rate ranging from 4.9% to as much as 69.6%. This shows that the elderly subjects in general had a high acceptance toward the collection of demographic data, information about their medical history, and bio-measurement data, thereby resulting in a low data missing rate for profile features. On the other hand, the high data missing rate with health assessment features is consistent with the general situation in primary care. According to the frontline health care staff of the clinic, data could be missed because subjects were absent from scheduled appointments, unable to recall specific events that happened in the past, or declined to respond to questions that they felt uncomfortable to answer or considered sensitive.

TABLE 1

Statistics of the features with missing data.

| Percentage of missing data | Number of features |
| --- | --- |
| 0% | 96 |
| 1%-9% | 49 |
| 10%-19% | 22 |
| 20%-29% | 6 |
| 30%-39% | 97 |
| 40%-49% | 5 |
| 50%-59% | 152 |
| 60%-69% | 140 |

Experimental Outline

The DNN model was trained following the algorithm shown in FIG. 1A. Accordingly, applying the KNN imputation method noted above, $n_c$ was 96 and $n_s$ was 471; and the missing data was imputed to "fill in the crosses" in the data in an exemplary embodiment of the present disclosure; with reference to FIG. 2A using the algorithm described and depicted above with reference to FIG. 2B.

In the present disclosure, Euclidean distance was employed as the distance metric; however, other distance metrics (eg, City Block Distance, Cosine similarity, L1 distance, L2 distance, and Manhattan distance) can also be used.

Thereafter, NN1 and NN2 were used to learn the latent profile representations and latent health assessment representations, respectively, which were concatenated to yield the final representations for classification.

The trainable parameters of NN1 and NN2 that minimize the cost-sensitive classification loss in equation 8 were identified using the stochastic gradient descent (SGD) algorithm in a manner familiar to persons skilled in the art.

After the model converged, the optimized parameters were employed to generate the final representations and predict the probabilities of high-risk cases for the testing samples.

Performance Evaluation

The performance of the proposed DNN model was evaluated by making comparisons with five kinds of conventional algorithms (ie, logistic regression [LR], DT, RF, SVM, and single neural network [SNN]).

For SVM, three kernel functions were used (ie, linear, polynomial, and radial basis functions, denoted as SVM (linear), SVM (poly) and SVM (RBF), respectively. The SNN, employing all features in one shot as the input, was used to evaluate the effect of introducing an additional neural network in the proposed DNN on classification performance. Moreover, the effect of using CSL to tackle class imbalance was studied by applying it to the algorithms. The corresponding algorithms were denoted as LR+CSL, DT+CSL, RF+CSL, SVM (linear)+CSL, SVM (poly)+CSL, SVM (RBF)+CSL, SNN+CSL, and DNN+CSL. In summary, there were 16 algorithms overall under testing.

In the experiments, mean and KNN imputations were utilized to fill the missing data before model learning. The number of neighbors was set as k=5 for the KNN imputation. The LR, DT, RF, and SVM algorithms were implemented using the Scikit-Learn toolkit [43], where default settings were adopted for LR, DT, and the three versions of SVM models with different kernel functions.

In RF, the number of trees was set as 100 and the maximum depth of the trees was set as 3. For the DNN, the hidden dimensionalities for both NN1 and NN2 were set with the typical values of $d_1=128$ and $d_2=32$. Note that in the DNN, we concatenated the latent representations of NN1 and NN2 as the final representations.

To make SNN and DNN have the same final dimensionality, we set the hidden dimensionalities of SNN as twice of NN1 and NN2 (ie, $d_1=256$ and $d_2=64$).

All the neural network models were trained by the SGD with a momentum rate of 0.9 following common practice. While normalization to the range of 0 to 1 was initially applied to preprocess the input features, it turned out that the performance degraded instead. Hence, preprocessing methods were not applied in the experiments.

The algorithms under comparison were evaluated with 10-fold cross-validation. The records were randomly split into 10 folds of equal size. For each of the 10 runs, nine folds of records were employed as training samples and the remaining one fold of records was utilized as testing samples to evaluate prediction performance.

Four performance metrics were adopted, including area under the receiver operating characteristic curve (AUC), average precision (AP), sensitivity, and specificity. For imbalanced data sets, using classification accuracy as an evaluation metric would produce misleading results. Here, AUC was used instead as it is insensitive to class imbalance. The metric AP summarized the precision-recall curve by weighting the precision achieved at each threshold with the increase in recall at the previous threshold. Sensitivity is the recall of high-risk cases (ie, the proportion of "high-risk" testing samples that are accurately identified). Specificity is the recall of normal cases (ie, the proportion of "normal" testing samples that are accurately identified).

It was hypothesized that the performance of DNN+CSL would be better than that of the algorithms under comparison, which was tested by running pairwise one-sided t tests between DNN+CSL and each algorithm separately in terms of the four metrics. Furthermore, experiments were conducted to investigate variation in the performance of the DNN in terms of AUC and AP with the number of neighbors k when KNN imputation was used and with the dimensionalities $d_1$ and $d_2$ of the hidden layers in NN1 and NN2.

In addition, the effect of adding fully connected layers (FCLs) between the concatenated representation and the final prediction results was investigated. The experiment was conducted by adding one and two FCLs separately to the proposed DNN+CSL approach and evaluating the performance in terms of the four metrics.

Results Obtained

The results of the experiments conducted to evaluate the performance of the algorithms under comparison are shown in Tables 2 and 3, where the mean and SD of the four metrics over 10 runs are provided. In addition, the performance of the proposed DNN+CSL model was compared with that of the other algorithms using a pair-wise t test, and the corresponding P values are shown in the tables.

TABLE 2

Performance of algorithms with missing data handled by mean imputation.

| | Mean imputation | | | | | | | |
|---|---|---|---|---|---|---|---|---|
| Algorithms | AUC[a], mean (SD) | P value | AP[b], mean (SD) | P value | Sensitivity, mean (SD) | P value | Specificity, mean (SD) | P value |
| LR[c] | 0.82 (0.04) | .023 | 0.87 (0.03) | .047 | 0.50 (0.10) | <.001 | 0.91 (0.03) | >.99 |
| LR + CSL[d] | 0.82 (0.04) | .019 | 0.87 (0.03) | .030 | 0.67 (0.07) | .002 | 0.82 (0.02) | .98 |
| DT[e] | 0.65 (0.05) | <.001 | 0.76 (0.03) | <.001 | 0.43 (0.09) | <.001 | 0.87 (0.03) | >.99 |
| DT + CSL | 0.64 (0.02) | <.001 | 0.75 (0.03) | <.001 | 0.41 (0.05) | <.001 | 0.87 (0.02) | >.99 |
| RF[f] | 0.84 (0.05) | .52 | 0.89 (0.03) | .90 | 0.01 (0.01) | <.001 | 1.00 (0.00) | >.99 |
| RF + CSL | 0.84 (0.05) | .67 | 0.89 (0.03) | .93 | 0.64 (0.09) | .001 | 0.84 (0.03) | >.99 |
| SVM[g] (RBF[h]) | 0.78 (0.06) | <.001 | 0.85 (0.03) | <.001 | 0.12 (0.04) | <.001 | 0.99 (0.01) | >.99 |

TABLE 2-continued

Performance of algorithms with missing data handled by mean imputation.

| | Mean imputation | | | | | | | |
|---|---|---|---|---|---|---|---|---|
| Algorithms | AUC[a], mean (SD) | P value | AP[b], mean (SD) | P value | Sensitivity, mean (SD) | P value | Specificity, mean (SD) | P value |
| SVM (RBF) + CSL | 0.81 (0.05) | <.001 | 0.86 (0.03) | <.001 | 0.76 (0.08) | .98 | 0.73 (0.03) | <.001 |
| SVM (poly[i]) | 0.74 (0.06) | <.001 | 0.83 (0.03) | <.001 | 0.50 (0.07) | <.001 | 0.84 (0.03) | >.99 |
| SVM (poly) + CSL | 0.81 (0.05) | <.001 | 0.87 (0.03) | <.001 | 0.77 (0.08) | .99 | 0.73 (0.03) | <.001 |
| SVM (linear) | 0.79 (0.04) | <.001 | 0.85 (0.03) | <.001 | 0.48 (0.07) | <.001 | 0.89 (0.02) | >.99 |
| SVM (linear) + CSL | 0.80 (0.04) | .004 | 0.86 (0.03) | .005 | 0.65 (0.07) | <.001 | 0.81 (0.02) | .94 |
| SNN[j] | 0.81 (0.05) | <.001 | 0.87 (0.03) | <.001 | 0.32 (0.09) | <.001 | 0.95 (0.01) | >.99 |
| SNN + CSL | 0.81 (0.05) | <.001 | 0.87 (0.03) | <.001 | 0.65 (0.11) | .002 | 0.83 (0.02) | >.99 |
| DNN[k] | 0.83 (0.05) | .045 | 0.88 (0.03) | .13 | 0.33 (0.09) | <.001 | 0.96 (0.02) | >.99 |
| DNN + CSL | 0.84 (0.04) | N/A[l] | 0.88 (0.03) | N/A | 0.73 (0.09) | N/A | 0.80 (0.03) | N/A |

[a]AUC: area under the receiver operating characteristic curve.
[b]AP: average precision.
[c]LR: logistic regression.
[d]CSL: cost-sensitive learning.
[e]DT: decision tree.
[f]RF: random forest.
[g]SVM: support vector machine.
[h]RBF: radial basis function kernel.
[i]poly: polynomial kernel.
[j]SNN: single neural network.
[k]DNN: dual neural network.
[l]N/A: not applicable.

TABLE 3

Performance of algorithms with missing data handled by k-nearest neighbor imputation.

| | KNN[a] imputation | | | | | | | |
|---|---|---|---|---|---|---|---|---|
| Algorithms | AUC[b], mean (SD) | P value | AP[c], mean (SD) | P value | Sensitivity, mean (SD) | P value | Specificity, mean (SD) | P value |
| LR[d] | 0.81 (0.04) | .015 | 0.87 (0.03) | .10 | 0.46 (0.10) | <.001 | 0.91 (0.02) | >.99 |
| LR + CSL[e] | 0.81 (0.04) | .005 | 0.87 (0.02) | .028 | 0.65 (0.09) | .001 | 0.81 (0.03) | .90 |
| DT[f] | 0.67 (0.05) | <.001 | 0.77 (0.04) | <.001 | 0.48 (0.09) | <.001 | 0.86 (0.03) | >.99 |
| DT + CSL | 0.66 (0.07) | <.001 | 0.76 (0.05) | <.001 | 0.45 (0.13) | <.001 | 0.86 (0.02) | >.99 |
| RF[g] | 0.81 (0.04) | .004 | 0.87 (0.03) | .13 | 0.03 (0.04) | <.001 | 1.00 (0.00) | >.99 |
| RF + CSL | 0.81 (0.04) | .004 | 0.87 (0.03) | .020 | 0.68 (0.08) | .036 | 0.78 (0.02) | .10 |
| SVM[h] (RBF[i]) | 0.77 (0.06) | <.001 | 0.84 (0.03) | <.001 | 0.08 (0.04) | <.001 | 0.99 (0.01) | >.99 |
| SVM (RBF) + CSL | 0.80 (0.05) | <.001 | 0.86 (0.03) | <.001 | 0.75 (0.09) | .90 | 0.73 (0.02) | <.001 |
| SVM (poly[j]) | 0.75 (0.04) | <.001 | 0.83 (0.03) | <.001 | 0.50 (0.10) | <.001 | 0.86 (0.02) | >.99 |
| SVM (poly) + CSL | 0.81 (0.05) | <.001 | 0.86 (0.03) | <.001 | 0.74 (0.09) | .83 | 0.73 (0.02) | <.001 |
| SVM (linear) | 0.80 (0.04) | .001 | 0.86 (0.03) | .005 | 0.48 (0.11) | <.001 | 0.89 (0.02) | >.99 |
| SVM (linear) + CSL | 0.77 (0.04) | <.001 | 0.85 (0.02) | <.001 | 0.58 (0.11) | <.001 | 0.80 (0.02) | .75 |
| SNN[k] | 0.81 (0.06) | <.001 | 0.87 (0.04) | .006 | 0.33 (0.10) | <.001 | 0.95 (0.01) | >.99 |
| SNN + CSL | 0.80 (0.06) | <.001 | 0.86 (0.03) | <.001 | 0.65 (0.11) | .012 | 0.81 (0.03) | .90 |
| DNN[l] | 0.83 (0.05) | .039 | 0.88 (0.03) | .08 | 0.35 (0.09) | <.001 | 0.96 (0.01) | >.99 |
| DNN + CSL | 0.84 (0.04) | N/A[m] | 0.88 (0.03) | N/A | 0.72 (0.10) | N/A | 0.79 (0.04) | N/A |

[a]KNN: k-nearest neighbor.
[b]AUC: area under the receiver operating characteristic curve.
[c]AP: average precision.
[d]LR: logistic regression.
[e]CSL: cost-sensitive learning.
[f]DT: decision tree.
[g]RF: random forest.
[h]SVM: support vector machine.
[i]RBF: radial basis function kernel.
[j]poly: polynomial kernel.
[k]SNN: single neural network.
[l]DNN: dual neural network.
[m]N/A: not applicable.

As shown in Table 2, when mean imputation was applied, for the metrics AUC and AP, RF+CSL, RF, DNN, and DNN+CSL were the top performing algorithms.

For sensitivity, DNN+CSL was among the top three algorithms, with SVM (poly)+CSL and SVM (RBF)+CSL being the first and second algorithms, respectively, and RF exhibited the worst sensitivity (0.01). (Sensitivity is a measure of the proportion of subjects that are correctly identified as positive with respect to the total number of positive subjects—with the higher the better) For specificity, RF, SVM (RBF), and DNN were the top three algorithms. The specificity (ie portion of actual negatives, which got predicted as the negative (or true negative) of DNN+CSL reached 0.80.

Similar results were obtained for KNN imputation. As shown in Table 3, DNN+CSL, DNN, and RF were the top performing algorithms in terms of AUC and AP. DNN+CSL ranked third in sensitivity after SVM (RBF)+CSL and SVM (poly)+CSL.

The sensitivity of RF was the worst (0.03). The specificities of RF, SVM (RBF), and DNN were the best and that of DNN+CSL was 0.79.

The results also indicated that the performance of the algorithms evaluated by using mean imputation to tackle missing data was similar to that using KNN imputation. It can also be seen that when CSL was applied to tackle class imbalance, the sensitivity of the algorithms increased and specificity decreased.

Optimal Parameter Setting for the DNN

The effects of the parameters k, $d_1$, and $d_2$ on the performance of the proposed DNN in terms of AUC and AP are shown in FIGS. 3A, 3B, 4A, 4B, and 5A, 5B respectively.

Figures 3A, 3B:
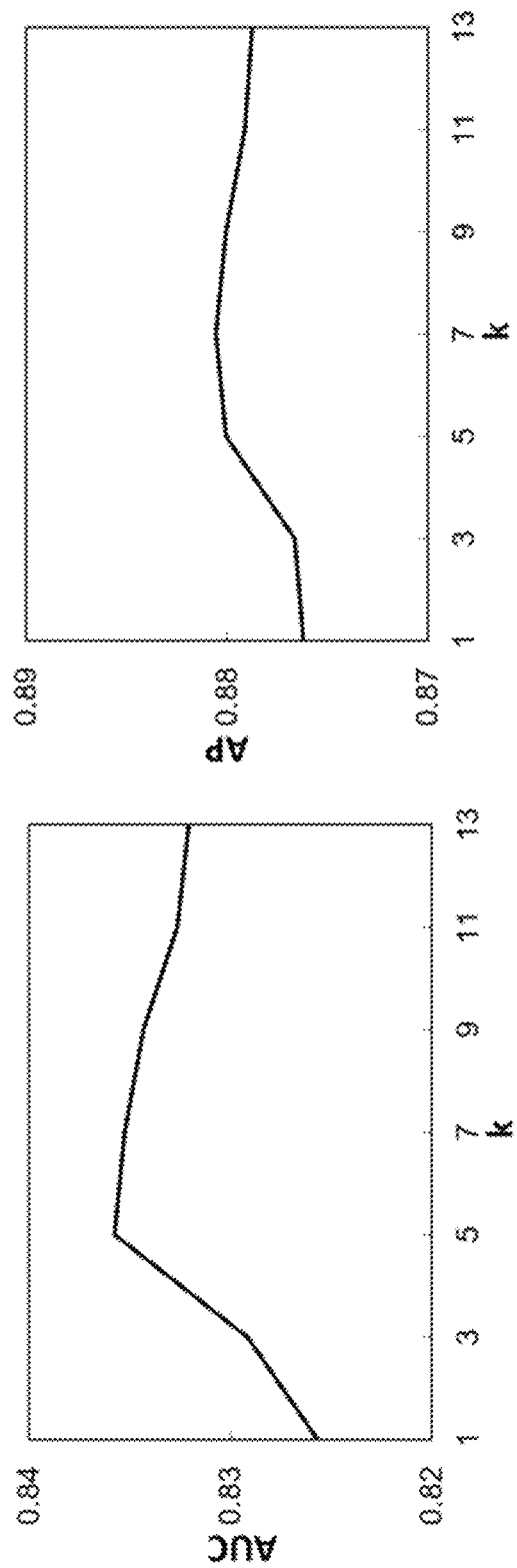
FIG. 3A depicts a plot of change in the area under curve (AUC) against various values of K in the KNN imputation process.
FIG. 3B depicts a plot of change in the average precision against various values of K in the KNN imputation process

It can be seen from FIG. 3A, B that when KNN imputation was used, both AUC and AP increased with k for k<5. When k was further increased, AUC exhibited a decreasing trend, (FIG. 3A) whereas AP remained at about the same level (FIG. 3B). This suggests that it is appropriate to set the number of neighbors as k=5 for KNN imputation.

Figure 4B:
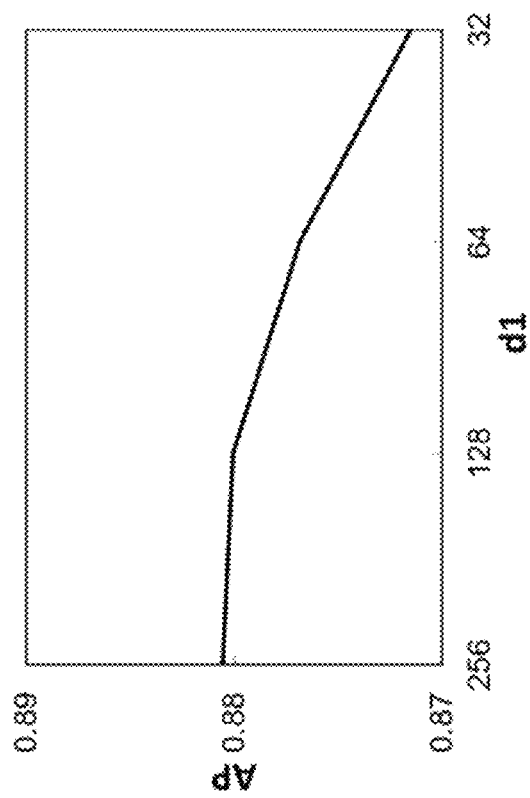
FIG. 4B depicts a plot of change in the average precision against various values of $d_1$ in the dimensions of the first hidden layer of the neural networks.
Figure 4A:
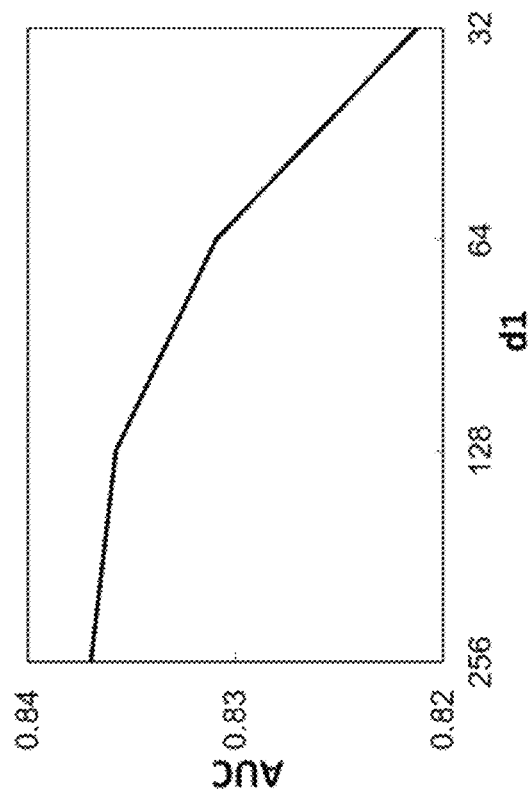
FIG. 4A depicts a plot of change in the area under curve (AUC) against various values of $d_1$ in the dimensions of the first hidden layer of the neural networks.
Figures 5A, 5B:
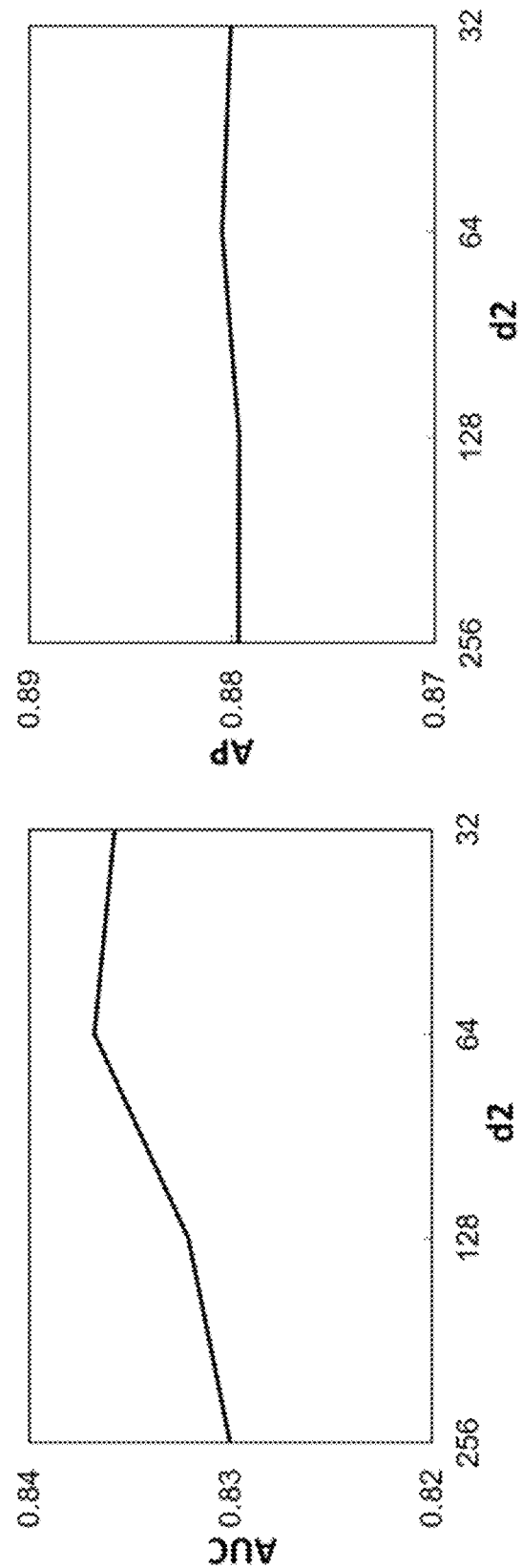
FIG. 5A depicts a plot of the change in area under curve (AUC) against various values of $d_2$ in the dimensions of the second hidden layer of the neural networks.
FIG. 5B depicts a plot of the change average precision against various values of $d_2$ in the dimensions of the second hidden layer of the neural networks.

For the number of dimensions $d_1$ of the first hidden layer of NN1 and NN2, as shown in FIG. 4A and FIG. 4B, a relatively large value (ie, 128 or 256) would yield a higher AUC and AP. In contrast, FIG. 5A and FIG. 5B show that setting the number of dimensions $d_2$ of the second hidden layer of NN1 and NN2 (in a specific embodiment of the disclosure) to a relatively small value (ie, 64 or 32) would achieve a higher AUC, while AP is insensitive to $d_2$.

The effect of adding fully connected layers (FCLs) to the proposed DNN+CSL model is shown in Table 4. For both mean and KNN imputations, it was found that adding one FCL lowered the AUC and specificity as compared with the finding without an FCL, whereas adding two FCLs lowered the AUC and specificity while increasing sensitivity.

TABLE 4

Effect of fully connected layers on the proposed dual neural network plus cost-sensitive learning model.

| Imputation | Algorithm | AUC[a], mean (SD) | AP[b], mean (SD) | Sensitivity, mean (SD) | Specificity, mean (SD) |
|---|---|---|---|---|---|
| Mean | DNN[c] + CSL[d] | 0.84 (0.04) | 0.88 (0.03) | 0.73 (0.09) | 0.80 (0.03) |
|  | DNN + CSL with one FCL[e] | 0.83 (0.04) | 0.88 (0.03) | 0.73 (0.09) | 0.79 (0.07) |
|  | DNN + CSL with two FCLs | 0.83 (0.05) | 0.88 (0.03) | 0.77 (0.11) | 0.75 (0.04) |
| KNN[f] | DNN + CSL | 0.84 (0.04) | 0.88 (0.03) | 0.72 (0.10) | 0.79 (0.04) |
|  | DNN + CSL with one FCL | 0.83 (0.04) | 0.88 (0.03) | 0.71 (0.10) | 0.77 (0.09) |
|  | DNN + CSL with two FCLs | 0.82 (0.05) | 0.87 (0.03) | 0.77 (0.12) | 0.74 (0.03) |

[a]AUC: area under the receiver operating characteristic curve.
[b]AP: average precision.
[c]DNN: dual neural network.
[d]CSL: cost-sensitive learning.
[e]FCL: fully connected layer.
[f]KNN: k-nearest neighbor.

Among the 16 algorithms under testing, DNN+CSL outperformed and consistently ranked among the top three algorithms in terms of AUC, AP, and sensitivity for both mean and KNN imputations.

In the case of KNN imputation, DNN+CSL indeed showed the best AUC (mean 0.84, SD 0.04) and AP (mean 0.88, SD 0.03), and ranked third in sensitivity (mean 0.72, SD 0.10).

The mean specificity of DNN+CSL reached 0.79 (SD 0.10).

Although RF was competitive and ranked among the top three algorithms in terms of AUC, AP, and specificity, the sensitivity was almost zero.

The results suggest that the proposed approach of deep learning with DNNs is apparently promising for screening cognitive impairment in elderly people and thus high-risk cases of dementia. This is attributed to the ability of the DNN to learn hierarchical latent representations from two types of data with different characteristics. The DNN approach is able to capture complex nonlinear relationships between input features and the output.

For both mean and KNN imputations, the performance of using two neural networks in the proposed DNN was better than that using a SNN in terms of AUC (P<0.001), AP (P<0.01), and sensitivity (P<0.01).

While the same features were adopted in both the DNN and SNN, the main difference was that for the DNN, the features were divided into two groups and fed into the two separate neural networks NN1 and NN2. As noted above, the inputs for NN1 were features concerning the profile, whereas the inputs for NN2 were features pertaining to the health assessment questionnaires as noted above.

Furthermore, since all the features were used indiscriminately in the SNN as the input, the characteristics of these two types of features could be interfered or diffused.

More importantly, it was likely that the health assessment features, whose quality was affected by missing data, could contaminate the profile features that were more complete and of better quality. This could be a reason for the suboptimal performance of the SNN as compared with the proposed DNN.

In the data set adopted, the ratio of high-risk to normal cases was 1 to 4.4. If the issue of class imbalance was ignored, the classification result would have been biased toward the majority class (ie, normal cases).

As a screening tool, high sensitivity is desirable as it is important to identify possible true positives (high-risk cases) and generate early signals, suggesting the potential need for a follow-up. CSL was thus proposed to remedy class imbalance.

The effectiveness was evident from the result that the sensitivity of most algorithms improved. For example, when mean imputation was applied, sensitivity increased by 118% for the DNN, 537% for SVM (RBF), and over 70 times for RF, whose sensitivity was almost zero (from 0.01 to 0.64). For missing data imputed using KNN, sensitivity increased by 109% for the DNN, 818% for SVM (RBF), and over 18 times for RF (from 0.03 to 0.68). The increase in sensitivity was achieved at the expense of specificity, with a moderate decrease of less than 26% for data imputed with both imputation methods. Nevertheless, the specificities of the algorithms were still above 0.73 when CSL was applied.

Figure 6:
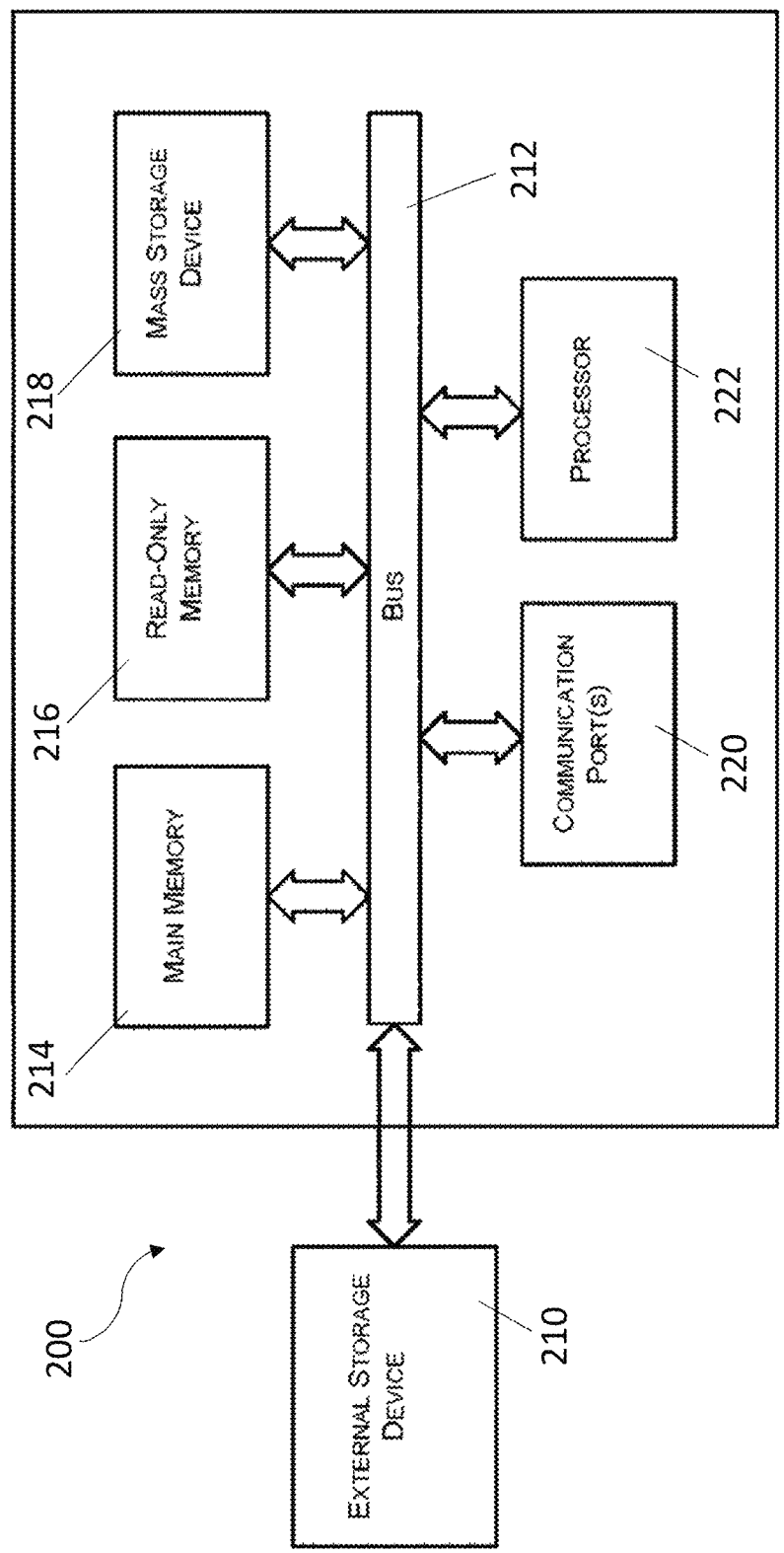
FIG. 6 depicts an exemplary computer system in which embodiments of the present invention may be utilized.

FIG. 6 depicts an exemplary computer system 200 in which embodiments of the present invention may be utilized. Computer system 200 includes an external storage device 210, a bus 212, a main memory 214, a read only memory 216, a mass storage device 218, a communication port 220, operatively connected to a processor 222.

Persons skilled in the art will appreciate that computer system 200 may include more than one processor 222 and communication ports 220. Examples of processor 222 include such processors as an Intel® processor(s), or AMD® or Athlon MP® processor(s), Motorola® lines of processors, FortiSOC™ system on a chip processors or other processors. Processor 222 may include various modules associated with embodiments of the present invention.

Optionally, communication port 220 can be any port such as a 10/100 Ethernet port, a Gigabit or 10 Gigabit port using copper or fiber, a serial port, a parallel port, or other ports. Communication port 220 may be chosen depending on a network, such a Local Area Network (LAN), Wide Area Network (WAN), or any network to which computer system connects.

Memory 214 can be Random Access Memory (RAM), or any other dynamic storage device commonly known in the art. Read only memory 216 can be any static storage device(s) including but not limited to, a Programmable Read Only Memory (PROM) chips for storing static information e.g. start-up or BIOS instructions for processor 222.

Mass storage 218 may be any mass storage solution, which can be used to store information and/or instructions. Exemplary mass storage solutions include, but are not limited to, Parallel Advanced Technology Attachment (PATA) or Serial Advanced Technology Attachment (SATA) hard disk drives or solid-state drives (internal or external, e.g., having Universal Serial Bus (USB) and/or Firewire interfaces).

Bus 212 is arranged to communicatively couple processor(s) 222 with the other memory, storage and communication blocks. Bus 212 can be, e.g. a Peripheral Component Interconnect (PCI)/PCI Extended (PCI-X) bus, Small Computer System Interface (SCSI), USB or the like, for connecting expansion cards, drives and other subsystems as well as other buses, such a front side bus (FSB), which connects processor 222 to software system.

Optionally, operator and administrative interfaces, e.g. a display, keyboard, and a cursor control device, may also be coupled to bus 212 to support direct operator interaction with computer system. Other operator and administrative interfaces can be provided through network connections connected through communication port 220. External storage device 210 can be any kind of external hard-drives, floppy drives, Compact Disc-Read Only Memory (CD-ROM), Compact Disc-Re-Writable (CD-RW), Digital Video Disk-Read Only Memory (DVD-ROM). Components described above are meant only to exemplify various possibilities.

The above embodiments are described by way of example only. Many variations are possible without departing from the scope of the disclosure as defined in the appended claims.

For clarity of explanation, in some instances the present technology may be presented as including individual functional blocks including functional blocks comprising devices, device components, steps or routines in a method embodied in software, or combinations of hardware and software.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, Universal Serial Bus (USB) devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The approach described herein has demonstrated promising performance in feature representation learning and the ability to capture different kinds of information relevant to the classification task when the two types of input features convey different information and have varied data distributions. Accordingly, the method and system of the disclosure demonstrate the potential to serve as a tool to screen for elderly people with cognitive impairment and predict high-risk cases of dementia at the asymptomatic stage, providing health care professionals with early signals that can prompt suggestions for a follow-up or a detailed diagnosis.

The approach of the present disclosure can be included as an important part of community healthcare information systems of elderly care centers, as a value-added feature where the dual neural network prediction algorithm could be scheduled to run on the records in the systems automatically and regularly to identify possible cases of high dementia risk. The information systems can then flag such cases for early attention by healthcare professionals.

The approach of the present disclosure has been demonstrated to effectively predict the score of Mini-Mental State Examination questionnaire which together with other tests such as laboratory tests, cognitive tests like MMSE, neuropsychological tests, CT/MRIO/PET scan and psychiatric tests, are used in clinical settings to assign subjects to a high risk class or normal risk class for developing dementia.

Advantageously, the assignment according to the disclosure of the present invention does not require to complete the questionnaire, which effectively avoids the practice effect that may occur due to the administration of examination at inappropriate timing or conditions. The screening by the approach of the present disclosure means that that the MMSE or other cognitive tests can be reserved until necessary.

The invention claimed is:

1. A machine learning method for predicting whether a specified subject is at high risk of developing cognitive impairment based upon a data record for the specified subject by automatically classifying the subject into a first class associated with a first predicted risk of cognitive impairment or a second class associated with a second predicted risk of cognitive impairment; wherein the method comprises:
   acquiring a plurality of subjects' records, wherein each record comprises a first data set of measured data and a second data set including results for two or more health assessment questionnaires and a label indicating that a subject of each record of the plurality of subjects' records belongs to the first class or the second class;
   automatically classifying subjects of the plurality of subjects into the first class or the second class according to the label;
   training a first neural network and a second neural network together on the plurality of subjects' records by generating representations thereof by iteratively:
   (i) generating by the first neural network a first representation of the first data set of a selected subject's record from the plurality of subjects' records; and
   (ii) generating by the second neural network a second representation for the second data set of the selected subject's record; and
   (iii) concatenating the first and the second representations together and using the concatenated first and second representations as inputs to a first classifier configured for assigning the selected subject's record to either the first class or the second class;
   (iv) updating trainable parameters of the first and second neural networks and the first classifier by confirmation with a classification made according to the label for the subject's record;
   predicting the risk of cognitive impairment for the specified subject by using the first classifier to evaluate a concatenated vector of the representations generated by the trained first and second neural networks respectively by assigning the specified subject by the first classifier to the first class or the second class;
   including a cost sensitive learning weighting to increase sensitivity of detection when using the first classifier for evaluating the concatenated representation of profile data and health assessment data and for updating the training parameters of the first and second neural networks;
   wherein the cost sensitive learning weighting $w_i$ associated with $i^{th}$ subject is calculated according to:

$w_i = m_r^n / m_r^d$ if $y_i = 1$ and $w_i = 1$ if $y_i = 0$ wherein:
   $m_r^n$ and $m_r^d$ are respectively numbers of normal cases and numbers of high-risk cases in plurality of subjects' records used for training the first network and second neural network; and
   $y_i$ is a ground-truth label of the training sample i;
   where $y_i = 1$ if the ground-truth label of the training sample i is high-risk; and
   where $y_i = 0$ if the ground-truth label of training sample i is normal.

2. The machine learning method according to claim 1 further comprising imputing incomplete data before determining by the first neural network of the representation for the specified subject's record or determining by the second neural network of the representation for the specified subject's record; wherein the determining is performed using one or more of K-nearest neighbour imputation or mean imputation.

3. The machine learning method according to claim 2 wherein imputing incomplete data before determining by the first neural network of the representation for the specified subject or determining by the second neural network of the representation for the specified subject's record is performed using K-nearest neighbour imputation wherein a set of the number of neighbours is specified as less than five.

4. The machine learning method according to claim 1, wherein a classification loss function L of the first classifier is calculated according to:

$$L = -\frac{1}{m_r} w_i \sum_{i=1}^{m_r} (1 - y_i)\log(1 - \hat{y}_i) + y_i \log(\hat{y}_i),$$

where $m_r$ is a number of training samples, and where $\hat{y}_i$ is predicted classification output probability.

5. The machine learning method according to claim 1 wherein the first neural network has two hidden layers which are arranged to determine the representation of the first data set of the subject's record which is learned layer by layer as follows:

$h_i^{p(1)} = \text{ReLU}(p_i W^{p(1)} + b^{p(1)})$ $h_i^{p(2)} = \text{ReLU}(h_i^{p(1)} W^{p(2)} + b^{p(2)})$ where $\text{ReLU}(\cdot)$ is a rectified linear unit activation function characterized by $\text{ReLU}(x) = \max(0, x)$, $p_i$ is an input profile feature associated with subject i, $h_i^{p(1)} \in R^{1 \times d_1}$ represents a representation of subject i, learned by the first hidden layer, and $h_i^{p(2)} \in R^{1 \times d_2}$ represents a latent representation of subject i, learned by the second hidden layer; and $d_1$ and $d_2$ are dimensionality of the first and second hidden layers respectively; $W^{p(1)} \in R^{np \times d_1}$ and $b^{p(1)} \in R^{1 \times d_1}$ are trainable parameters associated with the first hidden layer; and $W^{p(2)} \in R^{d_1 \times d_2}$ and $b^{p(2)} \in R^{d_1 \times d_2}$ are trainable parameters associated with the second hidden layer.

6. The machine learning method according to claim 1 wherein the second neural network has two hidden layers which are arranged to determine a representation of the second set of data including results for two or more health assessment questionnaires, which is learned layer by layer as follows:

$$h_i^{q(1)} = \text{ReLU}(q_i W^{q(1)} + b^{q(1)})$$

$$h_i^{q(2)} = \text{ReLU}(h_i^{q(1)} W^{q(2)} + b^{q(2)}),$$

where ReLU(·) is a rectified linear unit activation function characterized by ReLU(x)=max(0,x), where $q_i$ is a feature of health assessment of subject i and $h_i^{q(1)} \in R^{1 \times d_1}$ and $h_i^{q(2)} \in R^{1 \times d_2}$ are health assessment representations of subject i learned by the first and second hidden layers, and $d_1$ and $d_2$ are dimensionality of the first and second hidden layers respectively; and $W^{q(1)} \in R^{nq \times d_1}$, $b^{q(1)} \in R^{1 \times d_1}$, $W^{q(2)} \in R^{d_1 \times d_2}$, and $b^{q(2)} \in R^{1 \times d_2}$ are trainable parameters.

7. The machine learning method according to claim 1 wherein a stochastic gradient descent algorithm is used without normalisation to determine trainable parameters of the first and second neural networks.

8. The method according to claim 1 wherein dimensions of the first and second neural networks are identical.

9. The machine learning method according to claim 1 wherein the first data set in a subject record includes:
  demographic information of the subject selected from the group consisting of: gender, age, marital status, type of residency, relationship with roommates, and social participation;
  measurements conducted on the subject selected from the group consisting of: body temperature, pulse rate, oxygen saturation, blood pressure, and waist-hip ratio; and
  medical history selected from the group comprising records of health problems or past diseases.

10. The machine learning method according to claim 1 wherein the second data set in the selected subject's record includes results selected from the group of health assessment questionnaires consisting of: Brief Pain Inventory, Elderly Mobility Scale, Geriatric Depression Scale, Mini Nutrition Assessment, Constipation questionnaire, Roper Logan Tierney questionnaire, gross oral hygiene assessment, visual acuity assessment, and a survey of favorite activities questionnaire.

11. The machine learning method according to claim 1 wherein the specified subject's record comprises the first data set of measured data and the second data set including results for two or more health assessment questionnaires.

12. A machine learning method for training first and second neural networks to determine whether a specified subject is at high risk of developing cognitive impairment based upon a data record for the specified subject; the method comprising:
  acquiring a data record for a plurality of subjects, the data record including a first data set of measured data and a second data set including responses to two or more health assessment questionnaires, and a label indicating that the subject of the plurality of subjects having that data record belongs to a first class or a second class;
  automatically classifying each subject of the plurality of subjects into the first class or the second class according to the label;
  training the first and second neural networks together on the plurality of subjects' records by generating representations thereof by iteratively;
  (i) generating by the first neural network a representation of the first data set of a selected subject's record from the plurality of subjects' records; and
  (ii) generating by the second neural network a representation of the second data set of the selected subject's record; and
  (iii) concatenating the first and second representations together and using the concatenated representations as inputs to a first classifier configured for assigning the selected subject's record to either the first class or the second class;
  (iv) updating trainable parameters of the first and second neural networks and the first classifier by confirmation with a classification made according to the label for the subject's record
  using a cost sensitive learning weighting to increase sensitivity of detection when using the first classifier for evaluating the concatenated representation of profile data and health assessment data and for updating the training parameters of the first and second neural networks;
  wherein the cost sensitive learning weighting $w_i$ associated with $i^{th}$ subject is calculated according to:

$w_i = m_r^n / m_r^d$ if $y_i = 1$ and $w_i = 1$ if $y_i = 0$
  wherein:
  $m_r^n$ and $m_r^d$ are respectively numbers of normal cases and numbers of high-risk cases in plurality of subjects' records used for training the first and second neural network, and
  $y_i$ is a ground-truth label of the training sample i;
  where $y_i = 1$ if the ground-truth label of the training sample i is high-risk; and
  where $y_i = 0$ if the ground-truth label of training sample i is normal.

13. A tangible non transitory computer readable medium comprising instructions executable by a processor for executing a process of predicting whether a specified subject is at high risk of developing cognitive impairment based upon a data record for a specified subject by automatically classifying the specified subject into a first class associated with a first predicted risk of cognitive impairment or a second class associated with a second predicted risk of cognitive impairment; the data record for the specified subject including a first data set and a second data set including results for two or more health assessment questionnaires; the process comprising:
  acquiring a plurality of subjects' records wherein each record comprises the first data set of measured data and the second data set including results for two or more health assessment questionnaires, and a label indicating that the subject of each record belongs to the first class or the second class;
  automatically classifying each subject of a plurality of subjects into the first class or second class according to the label;
  training a first neural network and a second neural network together on health data of subjects of the plurality of subjects comprising assessment dataset and profile data respectively by:
    (i) generating by the first neural network a representation of the first data set for a subject;
    (ii) generating by the second neural network a representation for the subject's second data set;
    (iii) concatenating the representations together and using the concatenated representations as inputs to a first classifier configured for assigning the selected subject's record to either the first class or the second class;

(iv) updating trainable parameters of the first and second neural networks and the first classifier by confirmation with a classification made according to the label for the subject's record;

wherein a cost sensitive learning weighting is used to increase sensitivity of detection when using the first classifier for evaluating the concatenated representation of profile data and health assessment data and for updating the training parameters of the first and second neural networks; wherein the cost sensitive learning weighting $w_i$ associated with $i^{th}$ subject is calculated according to:

$$w_i = m_r^n / m_r^d \text{ if } y_i = 1$$

and $w_i = 1$ if $y_i = 0$ wherein:

$m_r^n$ and $m_r^d$ are respectively numbers of normal cases and numbers of high-risk cases in plurality of subjects' records used for training the first and second neural network, and $y_i$ is a ground-truth label of the training sample i;

where $y_i = 1$ if the ground-truth label of the training sample i is high-risk; and where $y_i = 0$ if the ground-truth label of training sample i is normal.

\* \* \* \* \*